United States Patent
Futami et al.

(10) Patent No.: US 9,081,877 B2
(45) Date of Patent: Jul. 14, 2015

(54) MEDICAL IMAGE INTERPRETATION SYSTEM

(75) Inventors: Hikaru Futami, Otawara (JP); Hiromasa Yamagishi, Otawara (JP)

(73) Assignees: Kabushiki Kaisha Toshiba, Tokyo (JP); Toshiba Medical Systems Corporation, Otwara-shi (JP)

( * ) Notice: Subject to any disclaimer, the term of this patent is extended or adjusted under 35 U.S.C. 154(b) by 1281 days.

(21) Appl. No.: 12/819,497

(22) Filed: Jun. 21, 2010

(65) Prior Publication Data

US 2011/0002515 A1 Jan. 6, 2011

(30) Foreign Application Priority Data

Jul. 2, 2009 (JP) ................................. 2009-157979

(51) Int. Cl.
*G06F 19/00* (2011.01)
*G06Q 50/24* (2012.01)
*G06T 7/00* (2006.01)

(52) U.S. Cl.
CPC ............ *G06F 19/322* (2013.01); *G06F 19/321* (2013.01); *G06F 19/3487* (2013.01); *G06T 7/0012* (2013.01)

(58) Field of Classification Search
None
See application file for complete search history.

(56) References Cited

U.S. PATENT DOCUMENTS

| 7,203,266 | B2* | 4/2007 | Fukuzawa | 378/4 |
| 7,630,531 | B2* | 12/2009 | Chui | 382/128 |
| 7,899,684 | B2* | 3/2011 | Fukatsu et al. | 705/2 |
| 7,949,167 | B2* | 5/2011 | Krishnan et al. | 382/128 |
| 8,051,386 | B2* | 11/2011 | Rosander et al. | 715/810 |
| 8,423,571 | B2* | 4/2013 | Moriya | 707/769 |
| 2005/0018891 | A1* | 1/2005 | Barfuss et al. | 382/131 |
| 2006/0228012 | A1* | 10/2006 | Masuzawa | 382/131 |
| 2007/0238948 | A1* | 10/2007 | Bartsch et al. | 600/407 |
| 2008/0052126 | A1* | 2/2008 | Sasai et al. | 705/3 |

(Continued)

FOREIGN PATENT DOCUMENTS

| CN | 1680963 A | 10/2005 |
| CN | 1873676 A | 12/2006 |

(Continued)

OTHER PUBLICATIONS

Chinese Office Action issued Sep. 27, 2012, in China Patent Application No. 201010223366.7.

(Continued)

*Primary Examiner* — Anita Coupe
(74) *Attorney, Agent, or Firm* — Oblon, McClelland, Maier & Neustadt, L.L.P.

(57) ABSTRACT

In embodiments, a medical image interpretation system has at least a medical image storing part, a medical image referring part, a medical record storing part, a process controlling part, an information extraction processing part, an image region specifying part, and an image processing part. The process controlling part specifies a medical image and extracts a medical record of a patient of the medical image. The information extraction processing part classifies terms on a sentence written in the medical record into predetermined types to structure the sentence, and extracts a region term from the structured sentence. The image region specifying part specifies the range of images showing a region corresponding to the region term from the medical image and specifies the position and range of the region. The image processing part displays at least the region position and range in a visually recognizable manner.

12 Claims, 12 Drawing Sheets

(56) References Cited

U.S. PATENT DOCUMENTS

| | | | |
|---|---|---|---|
| 2008/0155451 A1* | 6/2008 | Lundstrom et al. | 715/772 |
| 2008/0267481 A1* | 10/2008 | Nakamura | 382/131 |
| 2009/0087048 A1* | 4/2009 | Takahashi | 382/128 |
| 2011/0075901 A1* | 3/2011 | Nakamura | 382/128 |

FOREIGN PATENT DOCUMENTS

| | | |
|---|---|---|
| CN | 1891154 A | 1/2007 |
| CN | 101040801 A | 9/2007 |
| CN | 101166470 A | 4/2008 |
| CN | 101425186 A | 11/2008 |
| JP | 6-251005 A | 9/1994 |
| JP | 2005-301453 | 10/2005 |
| JP | 2006-181137 A | 7/2006 |
| JP | 2009-128053 A | 6/2009 |
| JP | 2009-129108 A | 6/2009 |

OTHER PUBLICATIONS

Hidefumi Kobatake et al., "Simultaneous Segmentation of Multiple Organs in Multi-Dimensional Medical Images", Working Papers of Grant-in-Aid for Scientific Research in 2003-2006, Mar. 2008, pp. 11-1-11-23 and 2 cover pages.

Akinobu Shimizu et al., "Medical image processing for multi-organ, multi-disease computer-aided diagnosis", The Institute of Electronics Information and Communication Engineers Technical Report, PRMU2006-17, MI2006-17, May 2006, 6 pages.

Combined Office Action and Search Report issued Aug. 7, 2013 in Chinese Patent Application No. 201010223366.7 with English translation of categories of cited documents.

Office Action issued Sep. 17, 2013 in Japanese Patent Application No. 2009-157979.

Office Action issued Apr. 14, 2014 in Chinese Patent Application No. 201010223366.7.

* cited by examiner

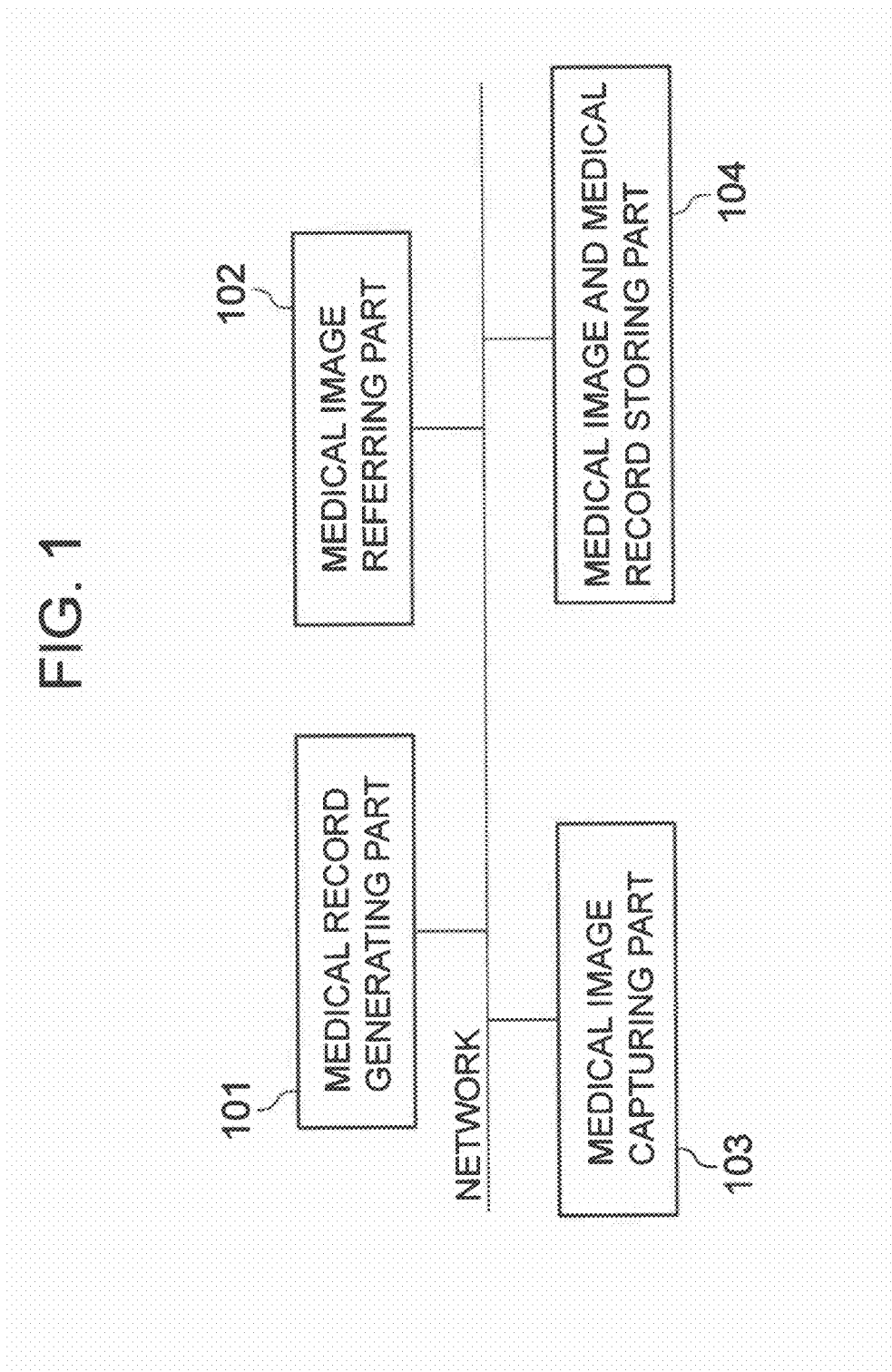

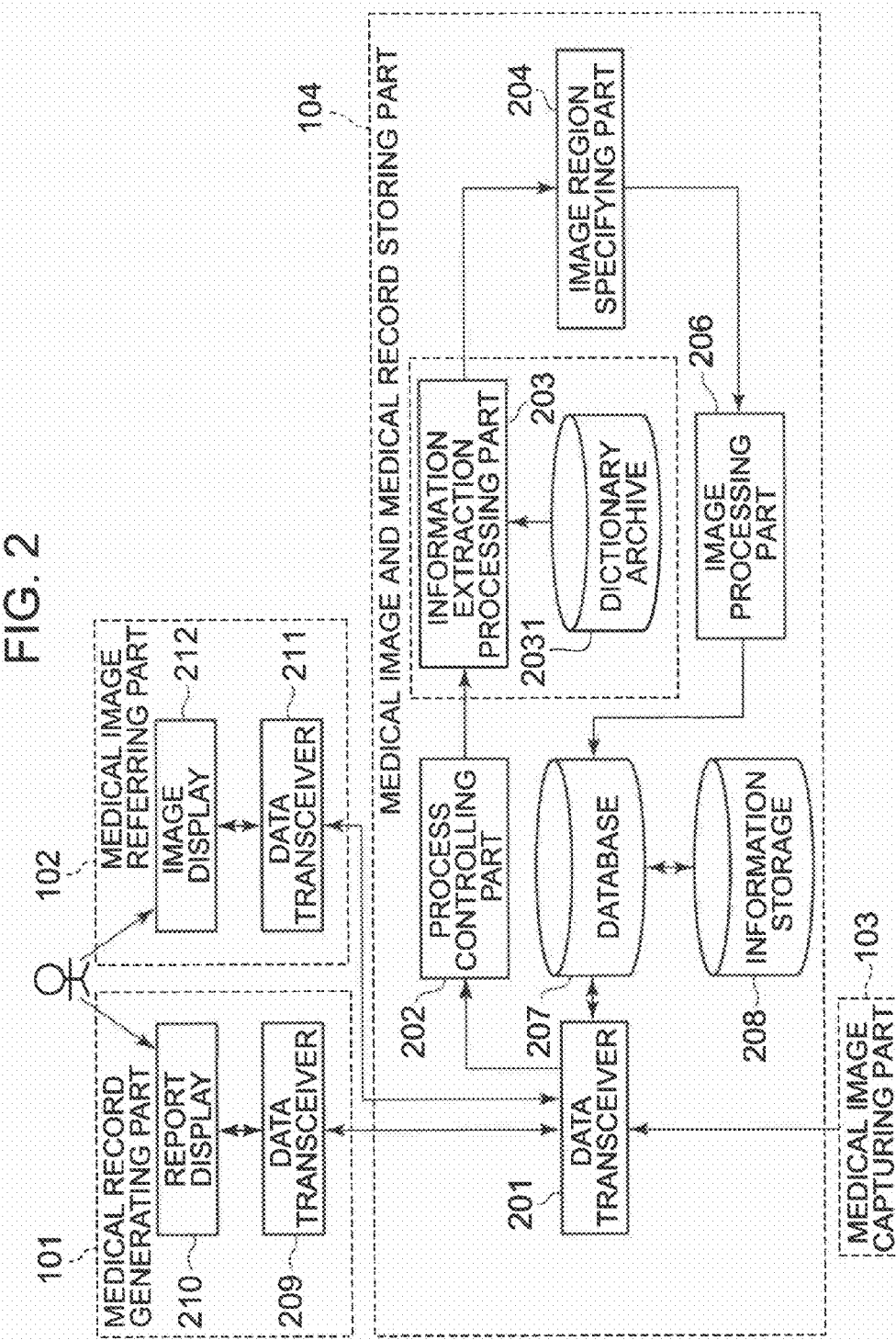

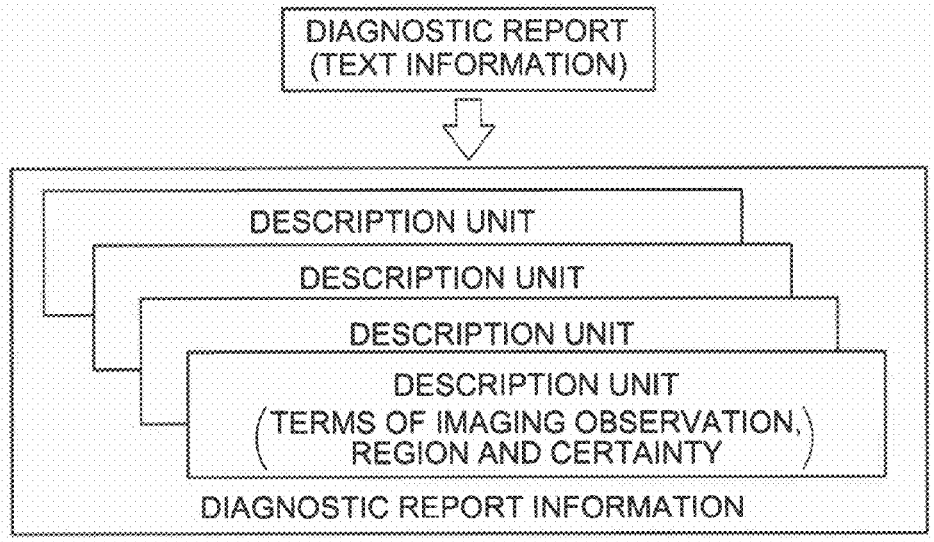
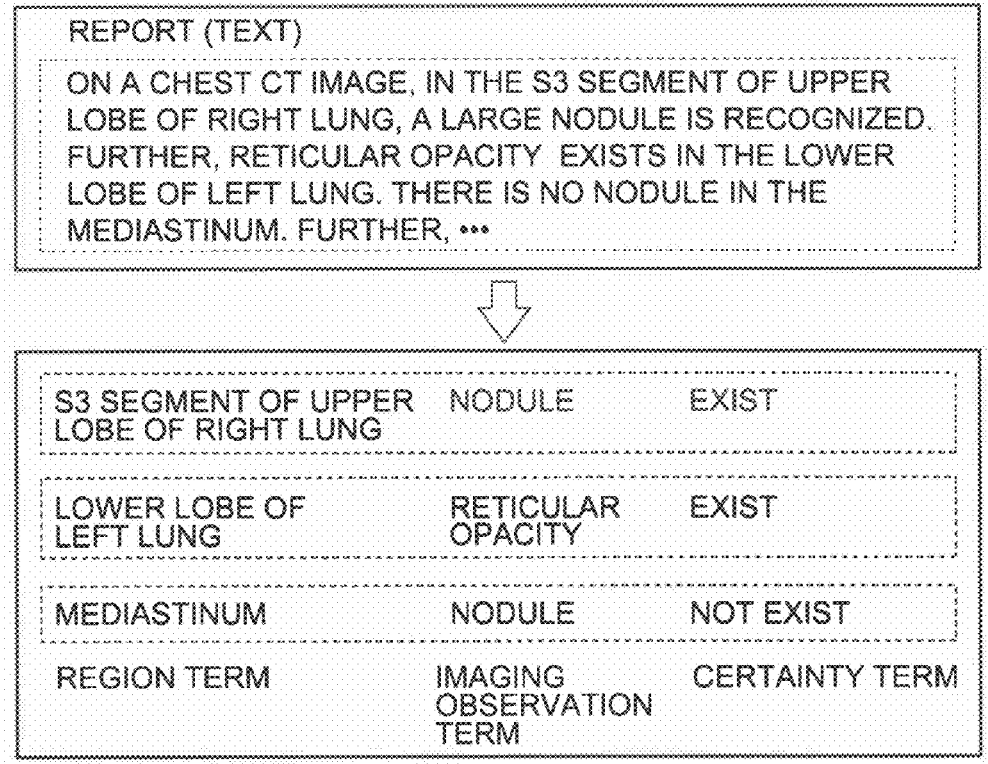

| REGION TERM | IMAGING OBSERVATION TERM | CERTAINTY TERM |
|---|---|---|
| S3 SEGMENT OF UPPER LOBE OF RIGHT LUNG | NODULE | RECOGNIZED |
| LOWER LOBE OF LEFT LUNG | RETICULAR OPACITY | NOT RECOGNIZED |
| RIGHT LUNG ZONE | INFLAMMATION | NOT SEEN |
| ... | ... | ... |

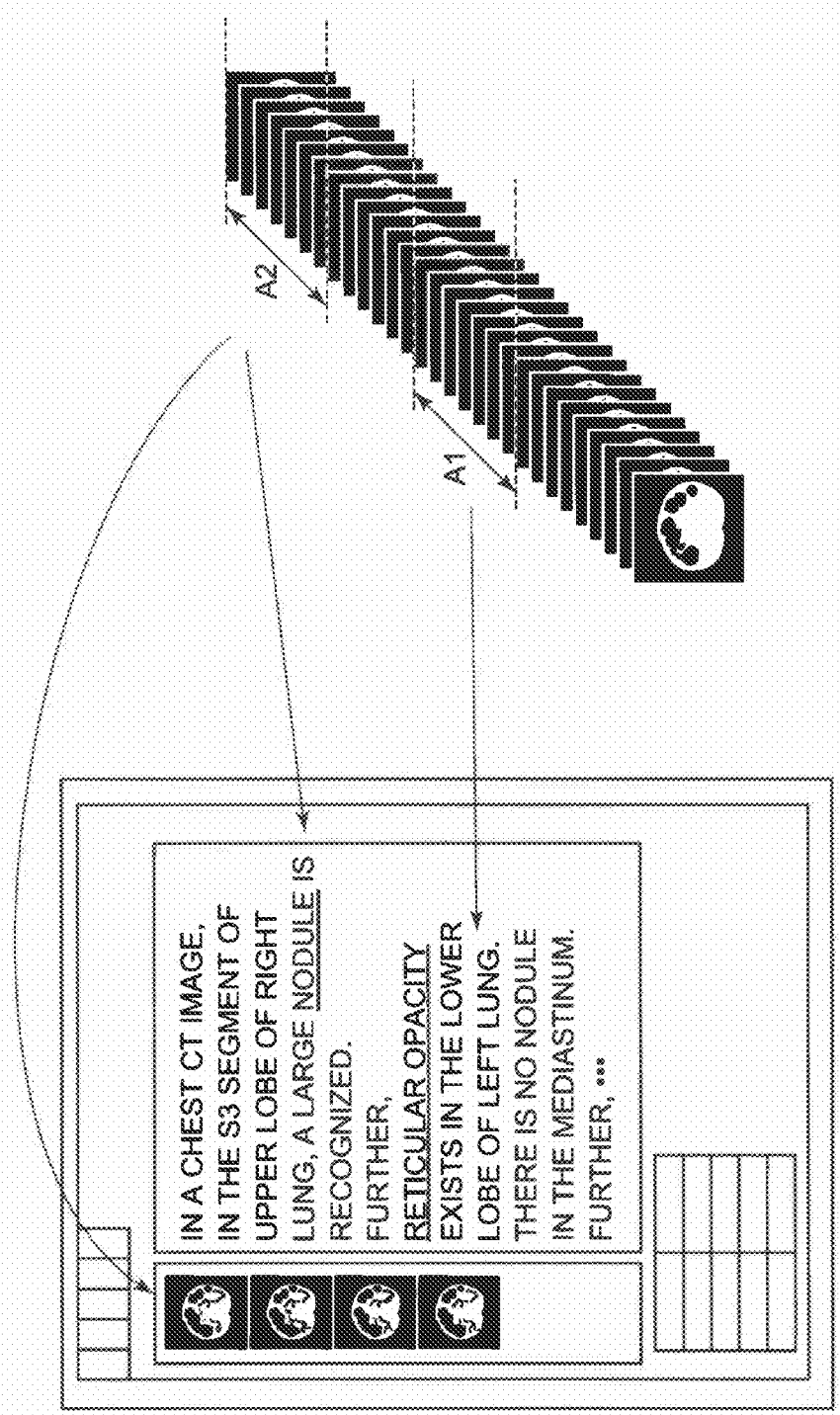

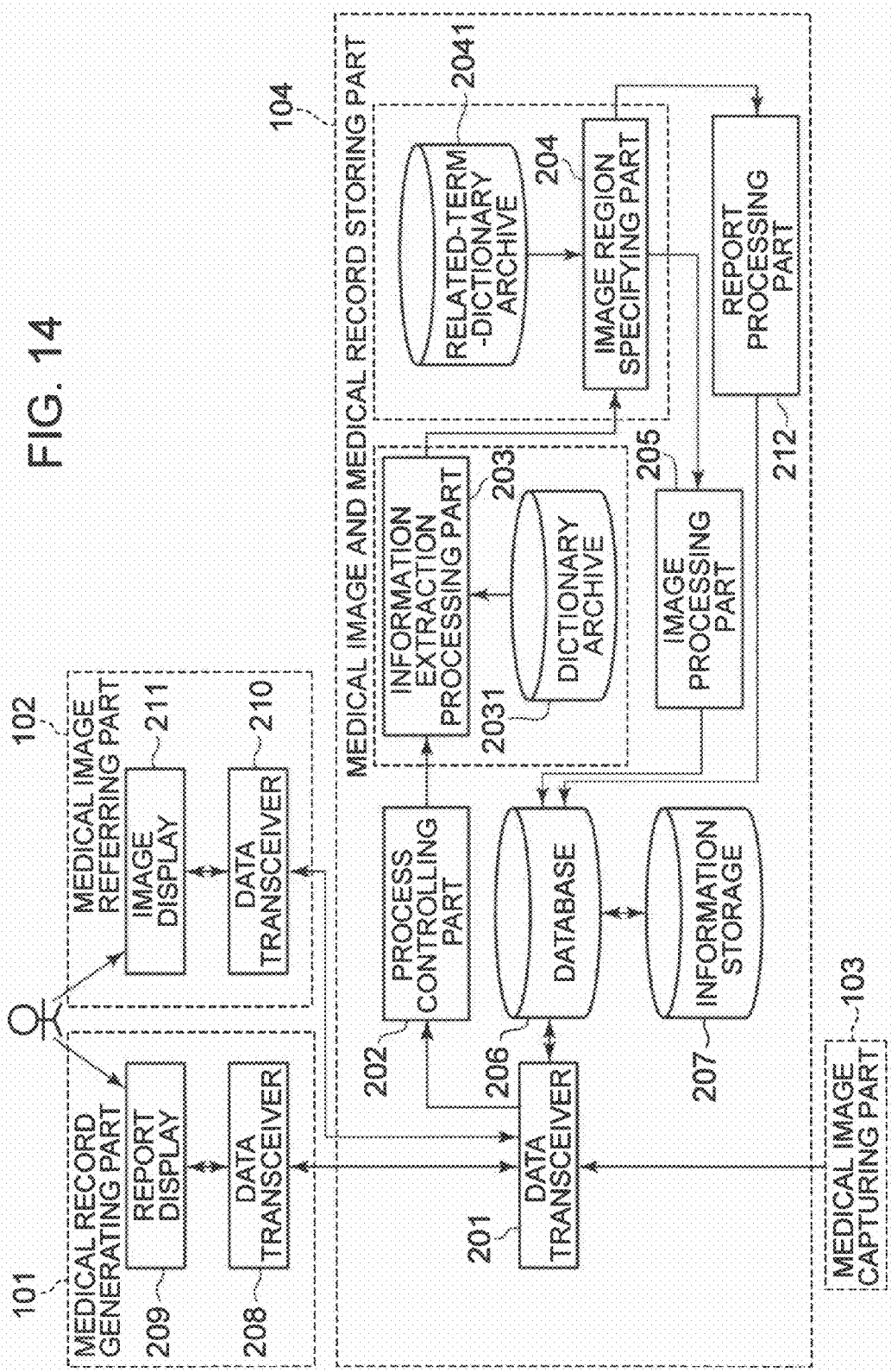

MEDICAL IMAGE INTERPRETATION SYSTEM

CROSS-REFERENCE TO RELATED APPLICATION

This application is based upon and claims the benefit of priority from Japanese Patent Application No. 2009-157979, filed on Jul. 2, 2009; the entire contents of which are incorporated herein by reference.

BACKGROUND

1. Field

Embodiments described herein relate generally to a medical image interpretation system in which a medical image storing apparatus that stores images of patients captured with a medical imaging device such as an X-ray computed tomography (CT) apparatus or a magnetic resonance imaging (MRI) apparatus, an image referring apparatus that allows a user to refer to the stored images, a medical record generating apparatus that generates medical finding reports on images, and a medical record referring apparatus that refers to the generated medical records are connected via a network.

2. Description of the Related Art

Conventionally, such a medical image interpretation system has been utilized that a medical imaging device, a medical image storing apparatus, an image referring apparatus, and a medical record generating apparatus are connected via a network. In this medical image interpretation system, interpretation of an image of a patient (a subject) captured with the medical imaging device (screening for a finding shown in an examination image) is performed, and a key image in the interpretation and a report on the result of the interpretation (a medical record such as a diagnostic report) are generated. In the following description, a diagnostic report as a medical record will be taken as an example.

In order to support generation of such a diagnostic report with a key image, a technique of linking a key image to a sentence relating to a finding in a diagnostic report is disclosed by Japanese patent application publication No. 2005-301453.

With regard to diagnostic reports, a key image is stored together with a diagnostic report for such a finding or diagnosis that seems to be important in an examination as described above, but a key image is not stored together with a diagnostic report for a finding or diagnosis other than the important one. Consequently, linked images can be specified for some of the findings and diagnoses described in diagnostic reports, and cannot be specified for some thereof.

Further, a segmentation technique of specifying the range of images showing anatomical regions (referred to as the "image range" hereinafter) from examination images and specifying the position and range of the region on the images (referred to as the "region position and range" hereinafter) is disclosed by the technical research report of the Institute of Electronics, Information and Communication Engineers (IE-ICE) Vol. 106, No. 74 (20060518), pp. 95-100 or Working Papers of Grant-in-Aid for Scientific Research (KAKENHI) (particular field research) by Ministry of Education, Culture, Sports, Science and Technology 2003-2006. However, the segmentation technique is not for selectively specifying a region described in a finding or diagnosis of a diagnostic report.

When performing interpretation of examination images captured for a patient having been searched for previously, a physician writes, into a diagnostic report on an image of a present examination, how a finding indicated in a diagnostic report on a previous examination has changed in a present examination. For this, the physician not only performs interpretation of the image of the present examination but also reads the previous diagnostic report to grasp the finding indicated therein and performs comparison interpretation with the image of the previous examination. In this case, for a finding or diagnosis written in the diagnostic report of the previous examination but provided with no specified key image, it is not clear for which of the images of the previous examination the finding or diagnosis is written. Therefore, the physician needs to perform re-reading not only for the images of the present examination but also for the images of the previous examination to search out an image showing the written finding or diagnosis. It takes time to perform this operation.

In particular, in a case that a physician who is not engaged in interpretation refers to a diagnostic report, it takes effort to search out a finding provided with no specified key image from among images.

BRIEF DESCRIPTION OF THE DRAWINGS

FIG. 1 is a configuration view showing an example of a system configuration.

FIG. 2 is a system block diagram of a medical image interpretation system relating to a first embodiment.

FIG. 3 is an explanation view of generating a description unit and structuring a diagnostic report.

FIG. 4 is a specific example of generation of a description unit from a description (a text) in a diagnostic report.

FIG. 13 is a view showing an example of linking a specified image (range) to a diagnostic report (for example, generating a hyperlink or pasting an image).

FIG. 14 is a system block diagram of a medical image interpretation system relating to a modified example.

DETAILED DESCRIPTION

Figures 5, 6:
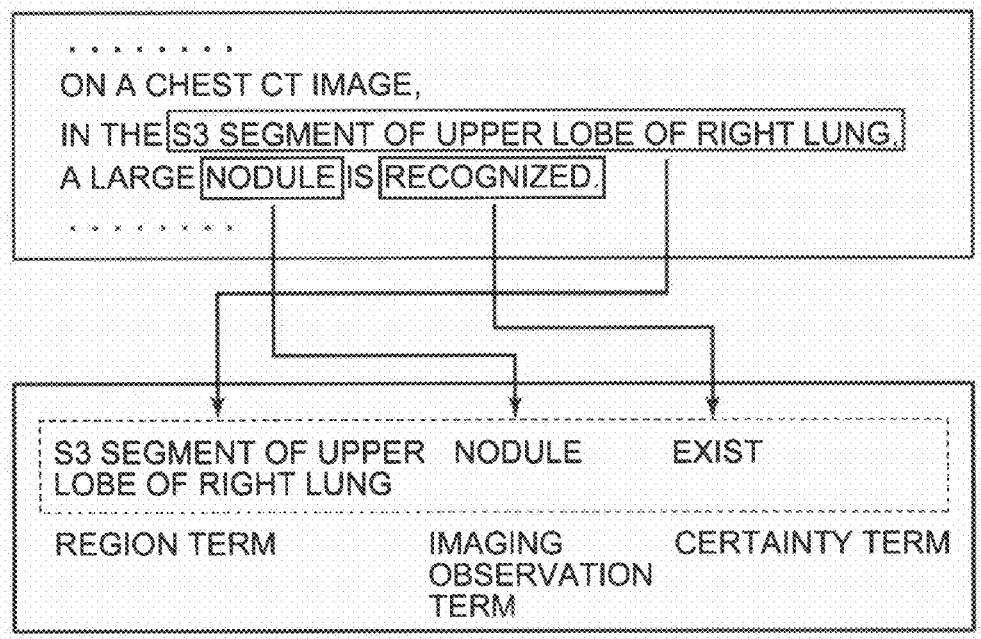
FIG. 5 is a data structure view showing the structure of dictionary data.
FIG. 6 is an explanation view for explaining the flow of information in generation of a description unit from a diagnostic report.

This embodiment is intended to facilitate identifying an image range showing regions described by a finding or a diagnosis of a diagnostic report related to images of the patient, and/or identifying a position and a range of the region in an image showing the region.

Further, this embodiment is intended to readably associate the image within the specified range with character strings described by the original diagnostic report about terms or information showing the region (hereinafter, referred to as region information).

In embodiments, a medical image interpretation system has at least a medical image storing part, a medical image referring part, a medical record storing part, a process controlling part, an information extraction processing part, an image region specifying part, and an image processing part. The process controlling part specifies a medical image and extracts a medical record of a patient of the medical image.

The information extraction processing part extracts terms for each sentence written in the medical record extracted by the process controlling part, classifies the terms for predetermined types to structure the sentence, and extracts a region term from the structured sentence. The image region specifying part specifies the range of images showing a region corresponding to the region term from the medical image, and specifies the position and range of the region on the images showing the region. The image processing part displays at least the region position and range so as to be visually recognizable.

First Embodiment

Below, a medical image interpretation system relating to a first embodiment will be described with reference to FIGS. 1 and 2.

Hereinafter, a "medical record" refers to data including text data of a finding or the like associated with a medical image, such as a diagnostic report and a medical chart. A "medical image" refers to an image of a patient captured with a medical imaging device, and may be composed of a plurality of images as an image captured with a CT or an MRI is, or may be composed of one image as an X-ray image is.

Hereinafter, a case will be explained in which the medical image is composed of a plurality of images. Below, a case of processing a diagnostic report as the medical record will be described as an example.

The medical image interpretation system relating to this embodiment specifies a region for which a finding or a diagnosis is written on a previous diagnosis report of a patient (hereinafter, the "finding" shall include the content of a diagnosis), and displays a place corresponding to the region on an examination image designated through a manipulation part (hereinafter, the "examination image" shall refer to the "medical image").

[Configuration]

First, components that configure the medical image interpretation system relating to this embodiment will be described.

FIG. 1 shows a typical configuration of the medical image interpretation system relating to this embodiment. In this configuration, a medical record generating part 101, a medical image referring part 102, a medical image capturing part 103, and a medical image and medical record storing part 104 are connected via a network.

In this configuration, an examination image is captured with the medical image capturing part 103, and the captured examination image is sent to and stored into the medical image and medical record storing part 104 as a digital image in the DICOM (Digital Imaging and COmmunications in Medicine) format. The examination image stored in the medical image and medical record storing part 104 is referred to with the medical image referring part 102. An operator generates a diagnostic report with the medical record generating part 101 while referring to the examination image with the medical image referring part 102.

In this configuration, it is desirable that communication between the respective blocks conforms to the DICOM, which is a medical image standard, but an existing standard may be applied as necessary.

Information communication is performed using the TCP/IP (Transmission Control Protocol/Internet Protocol), which is an industry standard. Data is exchanged by packet (a basic unit of transferred information) via the network.

FIG. 2 is a block diagram showing a detailed configuration of part of FIG. 1. With reference to FIG. 2, the configuration of the medical image interpretation system relating to this embodiment will be described in more detail.

Upon reception of an examination image from the medical image capturing part 103, a data transceiver 201 archives the examination image into a database 206 described later.

Further, at predetermined timing, for example, upon reception of a request from the medical record generating part 101 or the medical image referring part 102, the data transceiver 201 requests a process controlling part 202 to extract a region term and display the position and range of a region on the examination image (this request will be referred to as the "region display request" hereinafter).

Further, upon reception of the examination image from the medical image capturing part 103, the data transceiver 201 requests the process controlling part 202 to extract a region term (this request will be referred to as the "region extraction request" hereinafter).

Further, the data transceiver 201: receives a request from the medical record generating part 101, the medical image referring part 102, or the process controlling part 202; acquires information agreeing with conditions designated in the request, for example, conditions of a patient ID, examination date or modality, that is, data of a diagnostic report or an examination image or information for specifying a patient or an examination, from the database 206 and an information storage 207; and returns the information to the source of the request.

The process controlling part 202 has a part configured to extract information embedded in data to be processed (an image or diagnostic report), for example, information of a patient ID, examination data and modality, and search the database 206 described later via the data transceiver 201 to specify a patient and examination having information like the extracted information.

Further, upon reception of the region display request from the data transceiver 201, the process controlling part 202 controls: a process of extracting a region term from a diagnostic report by an information extraction processing part 203; a process of specifying the anatomical region position and range on an examination image by an image region specifying part 204; and a process of displaying the position and range of a region on an examination image by an image processing part 205. It is desirable that the respective processes are executed so as to be executed at the timing that the respective parts receive notification of completion of the last process.

Further, upon reception of the region extraction request from the data transceiver 201, the process controlling part 202 requests the image region specifying part 204 to execute the process of specifying the anatomical region position and range on the examination image, and controls the process.

The information extraction processing part 203 includes a dictionary archive 2031 in which dictionary data relating to terms representing a region and a finding are archived, and has a part configured to: compare a sentence written in a diagnostic report with the dictionary data stored in the dictionary archive 2031 and analyze the sentence; generate a data structure (this data structure will be referred to as a "description unit" hereinafter) to structure the diagnostic report (the structured report will be referred to as "structured report information" hereinafter); and extract a region term from the structured report information. Structuring of a diagnostic report and the description unit will be described below.

[Structuring of Report]

A process of structuring a diagnostic report and extracting a region term is executed in the following manner. For each sentence (referred to as a "sentence" hereinafter) written in a diagnostic report, terms are extracted while classified into a region term, a term (referred as an "imaging observation term" hereinafter) representing an imaging observation in a finding relating to the region term, and a term (referred to as a "certainty term" hereinafter) representing certainty of the finding. The extracted terms are combined for each sentence to generate a data structure called a description unit. The process is executed based on the description unit. FIG. 3 is an explanation view of generating description units and structuring a diagnostic report.

Since each sentence of a diagnostic report is analyzed to generate a description unit, one or more description units are generated from one diagnostic report. FIG. 4 shows a specific example of generation of description units from a description (a text) in a diagnostic report. In the example of FIG. 4, three description units are generated from three sentences included in the report (the text).

Below, a method for generating a description unit will be described with reference to FIGS. 5 and 6. FIG. 5 is a data structure view showing the data structure of the dictionary data stored in the dictionary archive 2031. Moreover, FIG. 6 is an explanation view for explaining the flow of information when a diagnostic report is structured and a data structure called a description unit is generated.

When extracting a term, the information extraction processing part 203 refers to the dictionary data in order to specify the term to be extracted. The dictionary data is archived in the dictionary archive 2031. As shown in FIG. 5, a number of terms are recorded in the dictionary data, falling into classifications of the region term, imaging observation term and certainty term. When the classification is designated, a term belonging to the designated classification is extracted. For example, when the region term is designated as the classification, the information extraction processing part 203 extracts a term classified into the region term, as a region term.

As shown in FIG. 6, the information extraction processing part 203 reads out an $N^{th}$ (N=1, 2, 3 . . . ) sentence from a finding field in a diagnostic report, performs a syntactic analysis of the read-out sentence by a technique such as a morphological analysis to divide the sentence into terms, and compares the respective terms archived in the dictionary data with the terms of the sentence while sequentially moving a comparison position from the beginning to the end of the data.

In a case that a term having been compared with the terms of the sentence is included in the sentence, the term is recorded so as to be included in a description unit for the scanned sentence.

By comparison of the respective terms recorded in the dictionary data, a region term, an imaging observation term, and a certainty term are extracted from one sentence. The extracted region term, imaging observation term, and certainty term are recorded as one set into a description unit. The explanation of the syntactic analysis technique is omitted herein.

In recording of a term into a description unit, the term to be recorded may be replaced with a typical term so as not to be influenced by various expressions. For example, in a case that a region term is described as "right S3," which has the same meaning as "S3 Segment of upper lobe of right lung," the term is recorded after being replaced with a typical term "S3 Segment of upper lobe of right lung." In the case of a certainty term, terms representing existence such as "recognized" and "seen" are recorded after being replaced with a typical term "exist," and terms representing nonexistence such as "not recognized" and "not seen" are recorded after being replaced with a typical term "not exist."

In the example of FIG. 6, "S3 Segment of upper lobe of right lung" is extracted as a region term, "nodule" is extracted as an imaging observation term, and "recognized" is extracted as a certainty term. A description unit is generated from the extracted terms as one set.

After structuring a diagnostic report, the information extraction processing unit 203 extracts region terms from description units included in structured report information. At this moment, after determination of other information (imaging observation terms or certainty terms) included in description units, a region term may be extracted from a description unit that agrees with a predetermined condition. For example, a region term may be extracted from a description unit that includes a term representing existence of a finding such as "seen," "recognized" or "exist" as a certainty term.

The image region specifying part 204 analyzes a series of images composing an examination image archived in information storage 207 (described later) or captured with the medical image capturing part 103 to three-dimensionally specify the anatomical region position and range, and outputs information that specifies the specified region position and range. For example, the image region specifying part 204 outputs, as the information specifying the region position and range, the image range (Z-coordinate) indicating from what number to what number of images the region is shown, or (a set of) coordinate information (XY-coordinates) indicating the region position and range on images showing the region, in pair with information referring to the region such as a region name.

The image region specifying part 204 uses the segmentation technique as a method for analyzing an examination image and specifying the range of images showing a region such as from $M^{th}$ to $N^{th}$ sheets (the image range) or the position and range of a region on images showing the region such as coordinate information and vector information (the region position and range).

For specification of a region, the image region specifying part 204 may receive a region term (right lung, left upper lobe or the like) as an input and specify only anatomical region positions and ranges that agree with the region term or specify all anatomical region positions and ranges included in a predetermined range such as an abdomen.

Further, when an examination image captured with the medical image capturing part 103 is archived into the information storage 207, the image region specifying part 204 may be configured to receive the region extraction request from the process controlling part 202, and specify all the anatomical region positions and ranges included in images of a predetermined range, from the examination image. In this case, the need for specifying the region position and range when receiving the region display request is eliminated, and a processing load in display of the region position and range is reduced.

It may be set in advance how fine the image region specifying part 204 specifies a region. For example, in the case of lungs, the image region specifying part 204 may specify right and left lungs, or upper, middle and lower lobes, or S1 to S9. Moreover, the setting may be changed by manipulation with a manipulator.

Further, the image region specifying part 204 may be configured to be capable of specifying the region position and range also in a case that an examination image is composed of one sheet of image. In this case, the image region specifying part 204 can be configured to output (a set of) coordinate information showing the position and range of the region shown on one sheet of image composing the examination image (information corresponding to the aforementioned XY-coordinates), in pair with information representing the region (for example, a region name). In this case, the image region specifying part 204 may be configured to link the one sheet of image to the region shown on the one sheet of image, as the image range (information corresponding to the aforementioned Z-coordinate).

The image processing part 205 links a region term extracted from a diagnostic report by the information extraction processing part 203 to three-dimensional position and range information of a region specified by the image region specifying part 204, and adds the region position and range corresponding to the region term extracted from the diagnostic report into an examination image as an annotation, an ROI (region of interest) or a marker.

Figure 8:
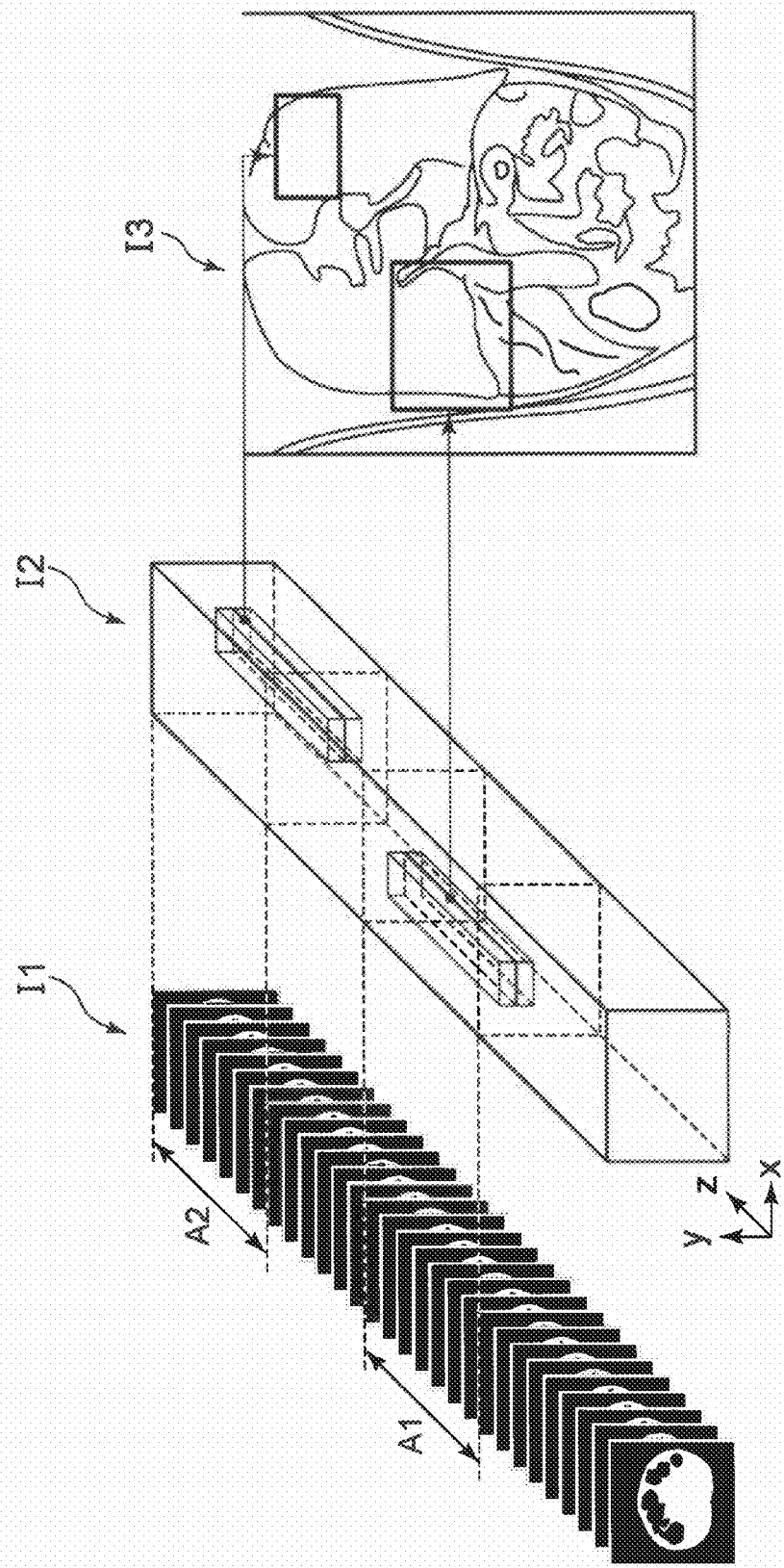
FIG. 8 is a schematic view showing the relation of the position and range detected from an image with the anatomical position and range of a region.

FIG. 8 is a schematic view showing a relation between a position and range detected from an examination image and an anatomical position and range of a region. In FIG. 8, 11 shows an examination image, 12 schematically shows three-dimensional position information of a region on the examination image, and 13 is an example of showing association of the position information of 12 with the anatomical position in an anatomical view. In FIG. 8, a region A1 represents the range of images of the lower of left lung. Moreover, a region A2 represents the range of images of the S3 segment of upper lobe of right lung. In the example of FIG. 8, the positions and ranges of the lower of left lung and the S3 segment of upper lobe of right lung having been three-dimensionally specified from the examination image by the image region specifying part 204 are shown in the anatomical view shown on the XZ plane.

Figure 9:
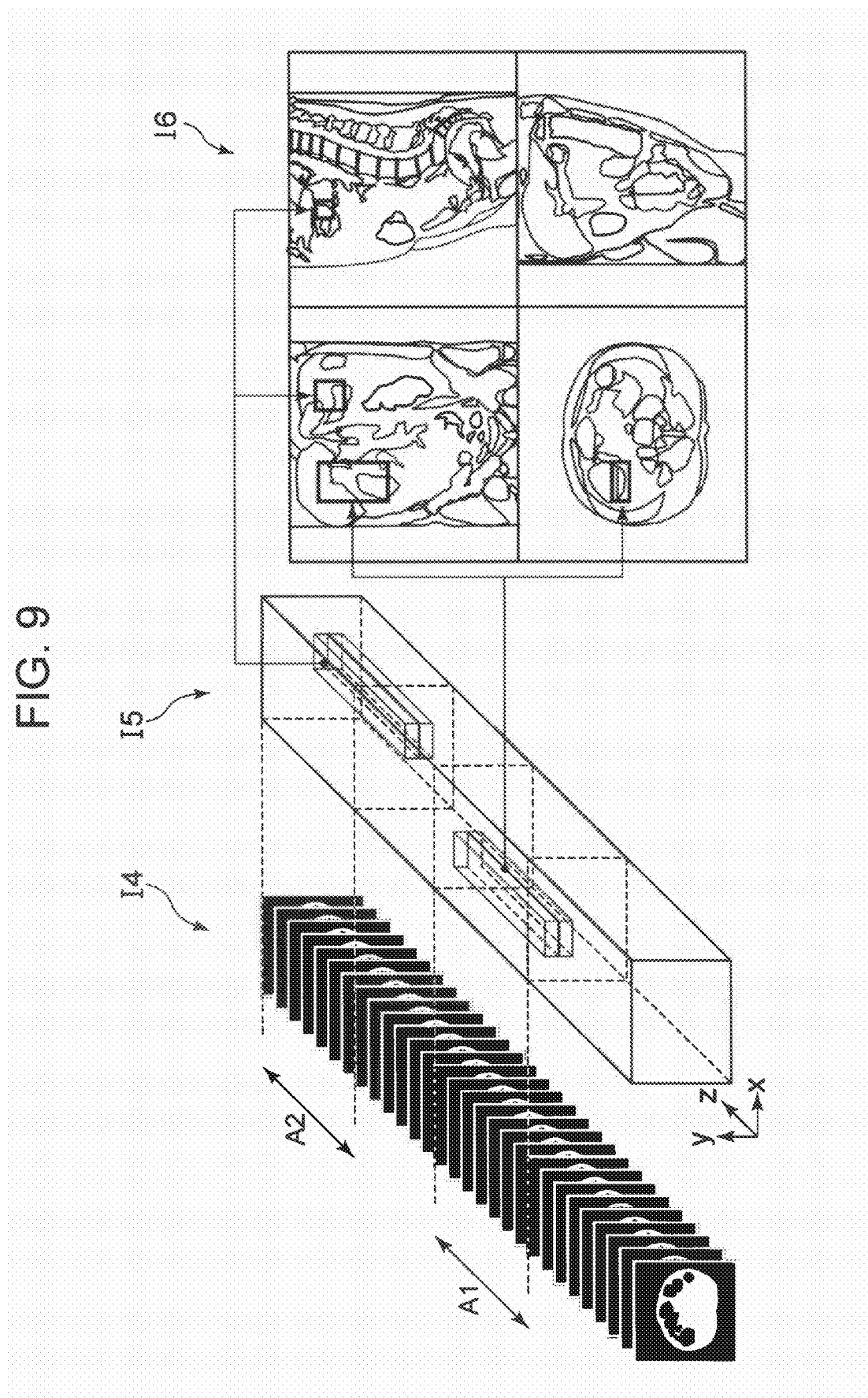
FIG. 9 is a display example of the detected position and range of an image.

FIG. 9 is an example of a display screen in a case that the region position and range extracted from a diagnostic report is displayed as an ROI on an examination image. In FIG. 9, 14 shows an examination image, 15 schematically shows three-dimensional position information of a region on the examination image, and 16 is an example of a display screen that displays the region position and range based on the position information of 15. In FIG. 9, a region A1 represents the image range of the lower of left lung. Moreover, a region A2 represents the image range of the S3 segment of upper lobe of right lung. Since the three-dimensional positions and ranges of the respective regions are held as coordinate information, it is possible to display the positions and ranges of the regions on the respective images shown on the XY plane, YZ plane and XZ plane.

The image processing part 205 stores data representing the image range and the region position and range added to an examination image, into the database 206. At this moment, the data to be stored may be data of an examination image including the image range and the region position and range.

Alternatively, excluding an examination image itself, only information for adding information representing the image range and the region position and range to the examination image, for example, only information representing in what range at what position in what image an ROI is to be displayed, such as coordinate information, may be stored in the database 206.

Further, for storing data of an annotation added to an examination image, the data may be made to be nonvolatile in the database 206. Alternatively, with the database 206 as temporary data storage, the data may be stored into the database 206 as temporary information for displaying the screen and discard the data when the data is no longer in use.

The database 206 is a database, and manages storage of data of an examination image or a diagnostic report, and supplementary information of data such as a patient ID, an examination date, series ID, image ID, report ID and modality.

Upon reception of data of an examination image or a diagnostic report, or supplementary information of the data, the database 206 archives into the information storage 207 (described later). The database 206 archives so that the data, the supplementary information and data, or the supplementary information is linked to an archive destination on the information storage 207.

Further, upon reception of a request to search for data of an examination image or a diagnostic report or supplementary information of the data, the database 206 acquires data or supplementary information that agree with a search condition included in the search request from the information storage 207, and returns to the requesting source.

The information storage 207 is an archive area in which real data of examination images and diagnostic reports are archived and managed.

In accordance with the condition designated by the operator via the report display 209, the data transceiver 208 generates a request to acquire a diagnostic report and transmits the acquiring request to the medical image and medical record storing part 104 (the data transceiver 201). Moreover, the data transceiver 208 receives data of the diagnostic report returned in response to the request to acquire the diagnostic report, from the medical image and medical record storing part 104 (the data transceiver 104), and causes a report display 209 to display the received data.

The report display 209 displays various kinds of information of a diagnostic report (the text information, patient ID, examination date, name of a department requiring an examination, and so on written in the report), and also serves as an interface for the operator (the physician) to manipulate.

Further, in a case that acquisition of a diagnostic report is designated by the operator (the physician) via the interface, the designated search condition is transmitted to the data transceiver 208, and acquisition of the diagnostic report is requested to display the content of the diagnostic report obtained consequently.

In accordance with the condition designated by the operator via an image display 211, a data transceiver 210 generates a request to acquire an examination image and transmits the acquiring request to the medical image and medical record storing part 104 (the data transceiver 201). Moreover, the data transceiver 210 receives data of an examination image returned in response to the request to acquire the examination image, from the medical image and medical record storing part 104 (the data transceiver 201), and causes the image display 211 to the received data.

The image display 211 displays an examination image and supplementary information (the patient ID, examination date, modality, and so on) of the examination image, and also serves as an interface (not shown) for the operator (the physician) to manipulate.

Further, in a case that acquisition of an examination image is designated by the operator (the physician) via the interface, the designated search condition is transmitted to the data transceiver 210, and acquisition of the examination image is also requested to display the examination image obtained consequently and the supplementary information of the examination image.

[Operation]

Next, with reference to FIG. 7, an operation of the medical image interpretation system relating to this embodiment will be described, assuming interpretation is executed on an image acquired in a present examination for a patient having been examined in the past.

Figure 7:
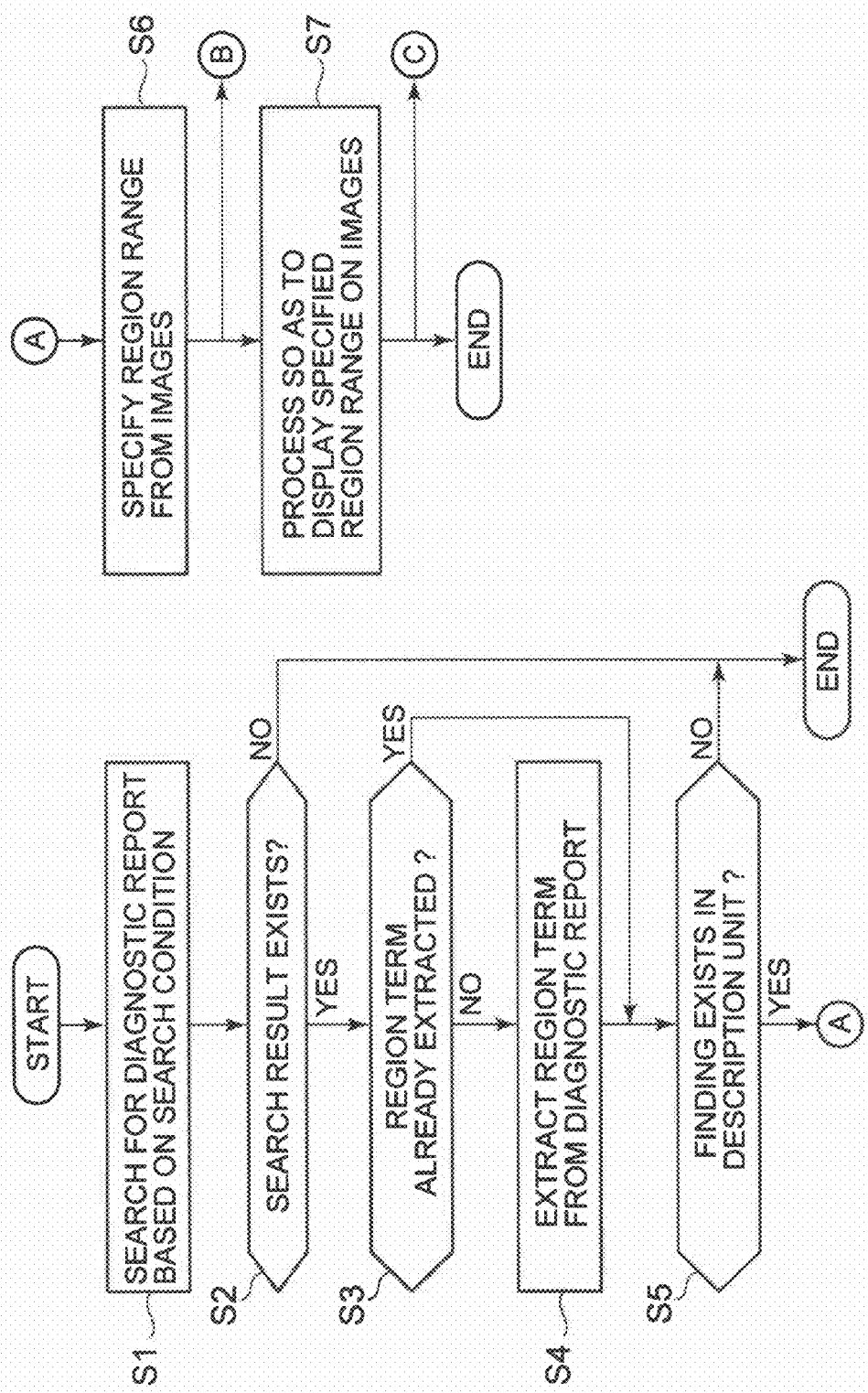
FIG. 7 is a flow chart showing an operation of the medical image interpretation system relating to the first embodiment.

FIG. 7 is a flow chart showing the operation of the medical image interpretation system relating to this embodiment.

Firstly, an examination image of the patient is captured with the medical image capturing part 103, and the examination image is transmitted to the medical image and medical record storing part 104.

Upon reception of the image from the medical image capturing part 103, the data transceiver 201 of the medical image and medical record storing part 104 registers supplementary information (the patient ID, patient name, gender, examination UID (Unique IDentifier), series UID (Unique IDentifier), and image UID (Unique IDentifier)) of the image into the database, and stores the examination image into the information storage 207.

When registering the supplementary information of the examination image into the database 206, the data transceiver 201 also requests the process controlling part 202 to specify a region on the examination image. In accordance with the request, the process controlling part 202 executes the process shown in FIG. 7.

(Step S1)

The process controlling part 202 searches the database 206 via the data transceiver 201 with supplementary information (for example, the patient ID) of an examination image as a search key, and searches for and specifies a diagnostic report of a patient to be examined generated in the past.

The diagnostic report search condition is changeable. The search condition may be set in the data transceiver 201 in advance, or the search condition may be changed by the operator's manipulation through the medical image referring part 102 or the medical record generating part 101.

The search conditions are, for example, diagnostic reports on images captured with the same kind of medical image capturing part as a present examination for a patient to be examined (for example, CT, MRI or the like; this kind will be referred to as a "modality" hereinafter), diagnostic reports on previous examinations up to two times before a present examination, and so on. These conditions may be combined as necessary.

(Step S2)

In a case that a diagnostic report satisfying the search condition does not exist (Step S2, No), the process ends at this point. In a case that a diagnostic report satisfying the search condition is detected (Step S2, Yes), the information extraction processing part 203 extracts a region term from the diagnostic report.

(Step S3)

Before extracting a region term, the information extraction processing part 203 firstly determines whether the region term has been extracted from the detected diagnostic report, that is, whether the diagnostic report has been structured.

Consequently, in a case that the diagnostic report has been structured and the region term has been extracted already (Step S3, Yes), the process of extracting the region term can be omitted.

For example, instead of extracting a region term after searching for a report as in this process, it is also possible to structure a diagnostic report and extract a region term in advance at the timing that the diagnostic report is generated. In this case, the need for the extraction of a region term after the search is eliminated, and it is possible to omit execution of a process as shown by branch of Step S3.

(Step S4)

In a case that a region term has not been extracted from a diagnostic report (Step S3, No), the information extraction processing part 203 generates a description unit from a text described in the diagnostic report to structure the diagnostic report, and extracts the region term from the generated description unit.

(Step S5)

Next, the image region specifying part 204 detects the position and range of images showing the region term extracted from the description unit, in the present examination image.

Firstly, the image region specifying part 204 specifies a description unit satisfying a predetermined condition from the diagnostic report. For example, in FIG. 7, the image region specifying part 204 checks a certainty term in the description unit and determines whether a term representing "exist" is registered. In FIG. 7, by determining a condition based on a certainty term, it is possible to extract only a region provided with a finding.

The condition for the determination can be information (a region term, an imaging observation term, or a certainty term) included in a description unit, and not limited to a certainty term. This condition may be set in the image region specifying part 204 in advance, or may be changed by the operator's manipulation. In a case that a description unit satisfying the condition cannot be detected, that is, in a case that a description unit including a certainty term representing "exist" cannot be detected in FIG. 7 (Step S5, No), the image region specifying part 204 immediately ends the process, so that the subsequent process steps will not be executed.

(Step S6)

In the case of detecting a description unit satisfying the condition, that is, a description unit including a certainty term representing "exist" in FIG. 7 (Step S5, Yes), the image region specifying part 204 specifies the position and range of a region indicated by a region term included in the description unit on the present examination image by using the segmentation technique, and outputs a set of information composed of the position and range information and the region term.

The position and range information can be information that allows specification of a range showing a target region on an examination image. For example, the position and range information includes the range of images showing the region (from $M^{th}$ to $N^{th}$ sheets), the position and range on images showing the region (coordinate information), and so on.

(Step S7)

After the image region specifying part 204 specifies the region position and range, the image processing part 205 processes the examination image in order to display the region range on the examination image. FIG. 9 shows an example of setting the specified region position and range as an ROI on the examination image and displaying on the screen.

Thus, it is possible to display the position and range of the region written in the previously generated diagnostic report as an annotation on the present examination image, and it becomes possible to visually grasp the region position and range on the present examination image for the finding indicated in the previous diagnostic report.

In extraction of a region term from a previous diagnostic report and specification of the region range, the processing target range may be narrowed down by designation of conditions, for example, by exempting a description to which a key image has already been linked from the processing target.

Second Embodiment

Figure 10:
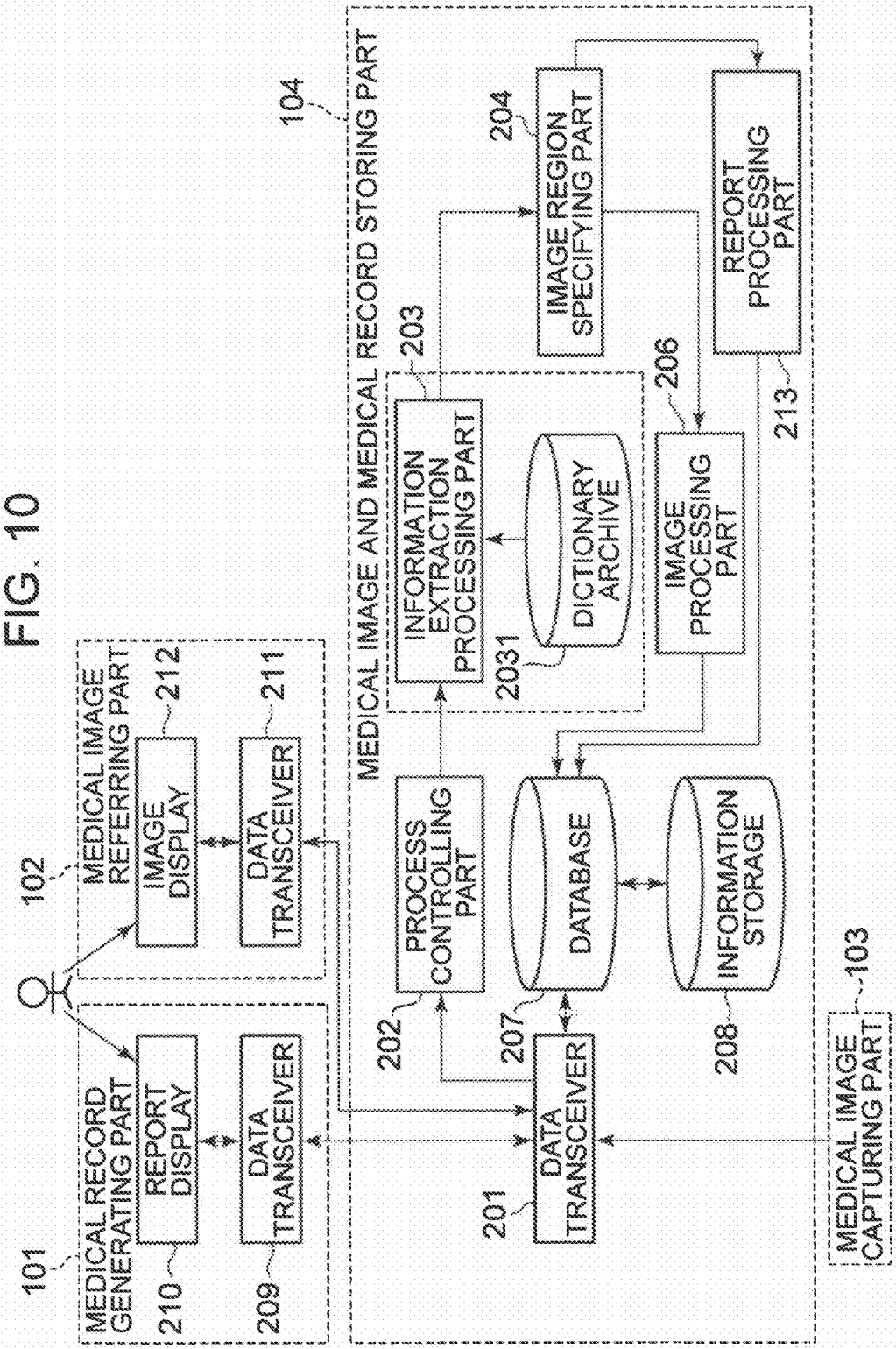
FIG. 10 is a system block diagram of an interpretation system relating to a second embodiment.

Next, a medical image interpretation system relating to a second embodiment will be described with reference to FIG. 10. FIG. 10 is a system block diagram of the medical image interpretation system relating to this embodiment. Below, a case of processing a diagnostic report as a medical record will be described as an example.

In the medical image interpretation system relating to this embodiment, while the operator (the radiologist) is generating a diagnostic report on a present examination image with the medical record generating part 101, the medical image interpretation system relating to this embodiment, at a point that a sentence being described is fixed, structures the sentence and extracts a region term, specifies the position and range of a region, and links images showing the region to the sentence or pastes the images to the diagnostic report.

[Configuration]

Firstly, components that configure the medical image interpretation system relating to this embodiment will be described, focusing on different parts from those of the first embodiment.

Upon reception of a generated diagnostic report or the content (the text) written in a diagnostic report from the medical record generating part 101, the data transceiver 201 specifies an examination image to be interpreted based on the supplementary information of the diagnostic report, transmits the received diagnostic report alone or together with the content thereof to the process controlling part 202, and requests the process controlling part 202 to extract a region term and link the examination image to the diagnostic report (this request will be referred to as a "report link request" hereinafter).

Upon reception of the aforementioned report link request from the data transceiver 201, the process controlling part 202 controls a process of extracting a region term from a diagnostic report by the information extraction processing part 203, a process of specifying the anatomical region position and range on the examination image by the image region specifying part 204, a process of displaying the region position and range on the examination image by the image processing part 205, and a process of linking the examination image to the diagnostic report by a report processing part 212. It is desirable that the respective processes are controlled so as to be executed at the timing that the respective parts receive notification of completion of the last process.

The report processing part 212 has a part configured to link a text described in a diagnostic report to an examination image. Thus, the report processing part 212 links an examination image including the range of the region specified by the image region specifying part 204 to the text on the diagnostic report relating to the region term extracted by the information extraction processing part 203. For link of the text to the examination image, the respective data can be linked so as to be referable. A typical method therefor is a hyperlink, for example.

In linking of an examination image to a text on a diagnostic report, an examination image including the range of a region term may be linked to a region term, or may be linked to another text in the source of generation of a description unit including a region term.

Further, the report processing part 212 pastes part or all of the images composing the examination image that include the range specified by the image region specifying part 204, to a predetermined position on a diagnostic report. In this case, real data of the examination image may be embedded into the predetermined position on the diagnostic report, or an icon representing the examination image (a reduced image of the examination image, for example) may be applied onto the diagnostic report to link a place in which the examination image is archived to the icon by using the hyperlink technique or the like.

FIG. 13 shows an example of linking of a specified image (range) to a diagnostic report (generating a hyperlink, pasting an image). In FIG. 13, a region A1 represents the image range of the lower of left lung. Moreover, a region A2 represents the image range of the S3 segment of upper lobe of right lung. In the example of FIG. 13, the image ranges of the "S3 segment of upper lobe of right lung" and "lower of left lung" are linked to terms of "nodule" and "reticular opacity" representing the findings relating to the respective regions. In an area located in the left part of the format of the diagnostic report, images of the examination image that include the range specified by the image region specifying part 204 are displayed in the thumbnail form.

[Operation]

Figure 11:
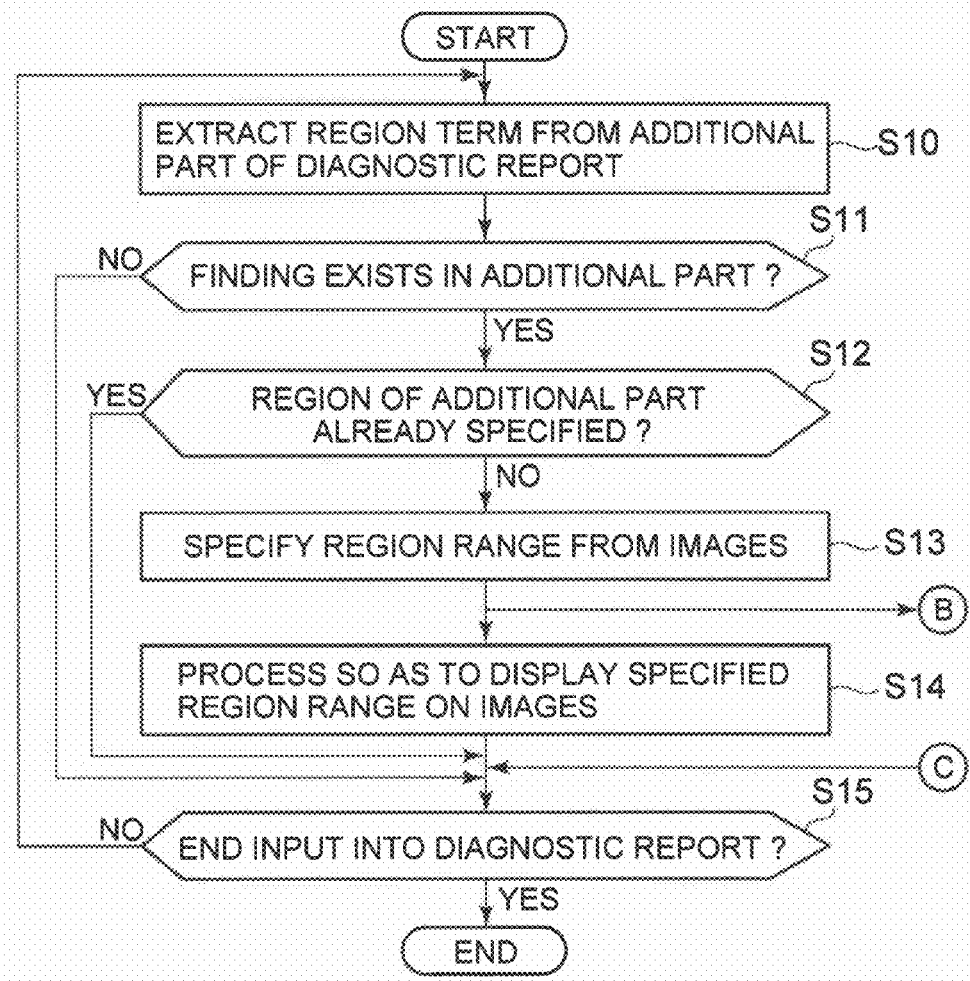
FIG. 11 is a flow chart showing an operation of the interpretation system relating to the second embodiment.
Figure 12:
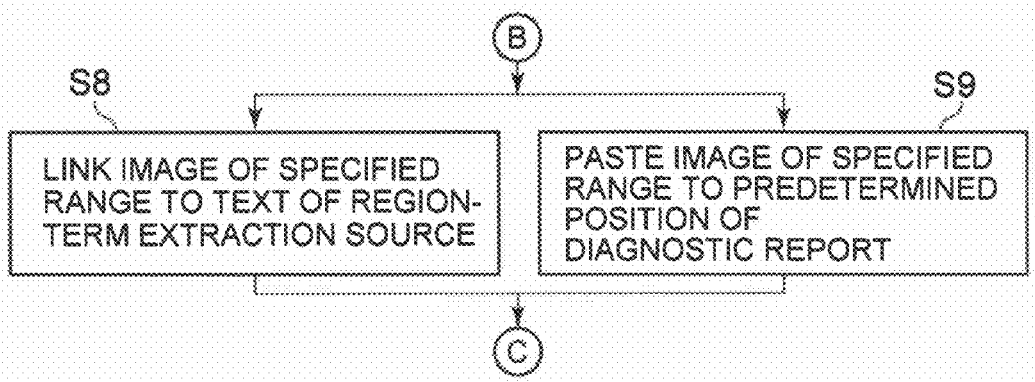
FIG. 12 is a flow chart showing an operation of linking an image to a diagnostic report in the interpretation system relating to the second embodiment.

Next, with reference to FIGS. 11 and 12, an operation of the medical image interpretation system relating to this embodiment will be described. FIG. 11 is a flow chart showing the operation of the interpretation system relating to this embodiment. FIG. 12 is a flow chart showing an operation of linking an image to a diagnostic report in the interpretation system relating to this embodiment.

When the operator (the radiologist) writes the content into a diagnostic report with the medical record generating part 101, information (text) inputted by the operator is sequentially transmitted to the data transceiver 201 of the medical image and medical record storing part 104 via the data transceiver 208.

The data transceiver 201 transmits the received input information (text) and the report link request to the process controlling part 202. The process controlling part 202 executes the processes shown in FIGS. 11 and 12 in accordance with the report link request.

(Step S10)

The process controlling part 202 sequentially transmits the received input information (text) to the information extraction processing part 203 and controls to extract a region term. When the received input information (text) is fixed as a sentence (fixed as one sentence by detection of a punctuation mark, for example), the information extraction processing part 203 structures the sentence by generating a description unit therefrom, and extracts a region term from the generated description unit.

(Step S11)

Next, the image region specifying part 204 detects the position and range of images showing the region term extracted from the description unit, in a present examination image. At this moment, only a description unit satisfying a predetermined condition is to be processed as in the medical image interpretation system relating to the first embodiment. Since the predetermined condition has been described in explanation of Step S5 of the medical image interpretation system relating to the first embodiment, the description thereof will be omitted in this embodiment.

In FIG. 11, a certainty term in a description unit is checked, and it is determined whether a term representing "exist" is registered. In a case that a description unit including a certainty term representing "exist" cannot be detected (Step S11, Yes), the subsequent process steps will not be executed.

(Step S12)

In a case that a description unit satisfying the condition, that is, a description unit including a certainty term representing "exist" is detected in FIG. 11 (Step S11, Yes), the image region specifying part 204 further determines whether the position and range of a region corresponding to a region term included in the description unit has been specified. In a case that the region position and range has been specified (Step S12, Yes), process steps (Steps S13, S14, S8 and S9) on this description unit will not be executed.

(Step S13)

In a case that the position and range of the region corresponding to the region term included in the description unit has not been specified (Step S12, No), the image region specifying part 204 specifies the position and range of the region represented by the region term included in the description unit by using the segmentation technique on the examination image referred to by the diagnostic report, and outputs a set of information composed of the information of the position and range and the region term. Since the content of the outputted data is the same as in Step S6 of the medical image interpretation system relating to the first embodiment, the description thereof will be omitted in this embodiment.

The outputted information may be archived in a temporary archive (not shown) so that the information may be loaded from the temporary archive for a region whose position and range has been specified. With the configuration of archiving the outputted information into the temporary archive, in a case that the position and the range have been detected, the need for executing a process of specifying the position and the region again is eliminated.

(Step S14)

After the image region specifying part 204 specifies the region position and range, the image processing part 205 processes the examination image in order to display the region range on the examination image. Since the content of the image processing is the same as in Step S7, the description thereof will be omitted in this embodiment.

(Step S8)

Next, the report processing part 212 links the position and range of the region specified by the image region specifying part 204 to the text on the diagnostic report corresponding to the input information from which the region term has been extracted. At this moment, the region position and range may be linked to the region term, or may be linked to a term (an imaging observation term) representing a finding in a description unit including the region term.

(Step S9)

The report processing part 212 pastes the region position and range specified by the image region specifying part 204, to a predetermined position of the diagnostic report. Alternatively, it is possible to configure so that the operator can select the region position and range pasted to the diagnostic report, and the text of the diagnostic report through the medical record generating part 101 and, in response to the manipulation by the operator, the report processing part 212 links the region position and range selected by the operator to the text of the diagnostic report.

(Step S15)

When the process on the fixed sentence is completed, it is determined whether the operation of inputting into the diagnostic report, that is, generating the report has ended. In a case that the operation of inputting into the diagnostic report has not ended (Step S15, No), transmission of the input information (text) from the medical record generating part 101 is waited again. In a case that the operation of inputting has ended (Step S15, Yes), the process ends.

Thus, while generating a diagnostic report, the operator (the radiologist) can sequentially refer to the position and range on the examination image of the region described in the diagnostic report being generated, and it becomes possible to link the displayed region position and range to the description on the diagnostic report by a simple operation.

Further, since the medical image interpretation system relating to this embodiment recognizes a description on a diagnostic report from which a region term has been extracted and information of the position and range on images displaying a region extracted from the description, it is possible, by configuring the medical image interpretation system to link the description of the diagnostic report to the region position and range, to eliminate the need for the link operation by the operator (the radiologist), and it becomes possible to largely simplify the linking procedure.

Further, although this embodiment describes for a present examination image, the region position and range may also be specified and displayed for a previous examination image. For example, by specifying and displaying the region position and range for both the present examination image and the previous examination image, it becomes possible to compare and interpret the present examination image and the previous examination image by a simple operation, for the region described in the diagnostic report.

Although, while the operator (the radiologist) is generating a diagnostic report, the medical image interpretation system sequentially displays the position and range of the region included in the description of the diagnostic report in this embodiment, it is also possible to extract a region written in the diagnostic report at the timing that generation of the diagnostic report is completed. This can be realized by combining the operation shown in FIG. 12 with the operation (FIG. 7) of the diagnostic report support system according to the first embodiment, and processing the generated diagnostic report at the time of the process of Step S1.

[Modification]

Next, a medical image interpretation system relating to a modification will be described with reference to FIG. 14. FIG. 14 is a system block diagram of the medical image interpretation system relating to this modification based on the configuration of the second embodiment. Below, a case of processing a diagnostic report as a medical record will be described as an example.

In the medical image interpretation system relating to the modification, the image region specifying part 204 includes a related-term-dictionary archive 2041. Thus, in a case that the image region specifying part 204 specifies the region position and range, it is also possible to process a term in a similarity relation or inclusion relation with a term of the target region and so on. Although the modification will be described based on the second embodiment, it is also possible to obtain the same effect by incorporating the related-term-dictionary archive 2041 into the configuration of the first embodiment.

[Configuration]

Firstly, components that configure the medical image interpretation system relating to the modification will be described, focusing on different parts from those of the first and second embodiments.

The related-term-dictionary archive 2041 has dictionary information representing the relation among terms, for example, the relation among terms in an inclusion relation indicating a superordinate concept or a subordinate concept of a certain term or a similarity relation such as synonyms of a certain term. Upon reception of a request to search for a related term together with a term to be searched about the relation (referred to as a "searched term" hereinafter) and information representing a relation (the inclusion relation or the similarity relation), the related-term-dictionary archive 2041 returns another term having the abovementioned relation with the searched term, as a related term.

Figure 15A:
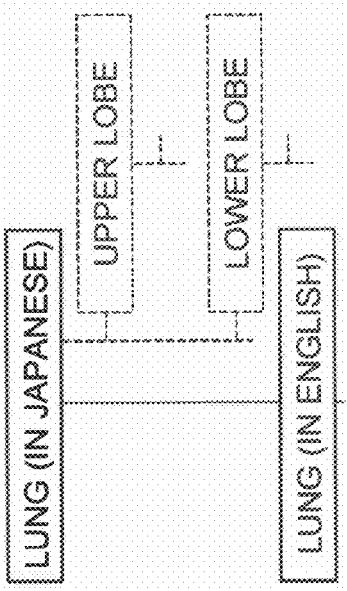
FIG. 15A is a schematic view for explaining an inclusion relation among terms in an anatomical classification.
Figure 15B:
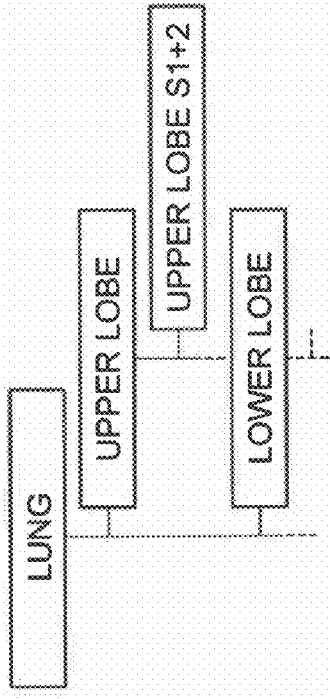
FIG. 15B is a schematic view for explaining an inclusion relation among terms in a pathological classification.
Figure 15C:
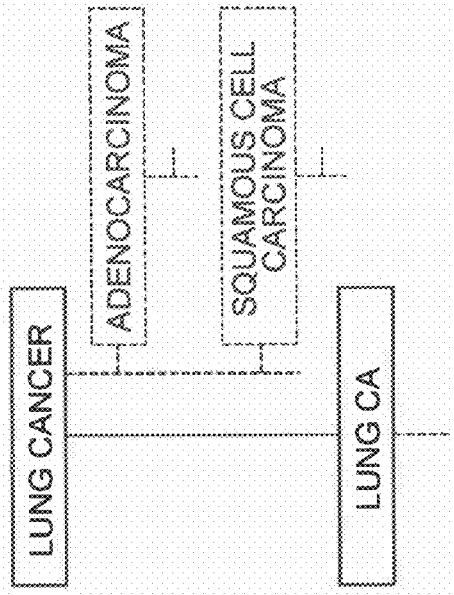
FIG. 15C is a schematic view for explaining a similarity relation among terms in the anatomical classification.
Figure 15D:
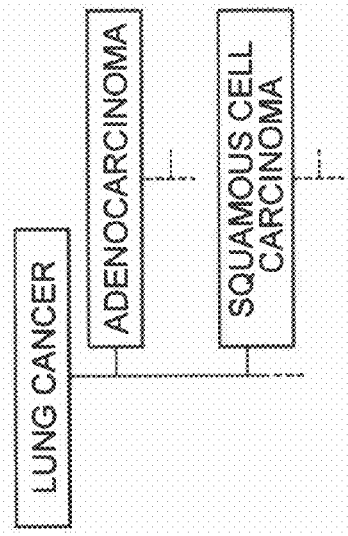
FIG. 15D is a schematic view for explaining a similarity relation among terms in the pathological classification.

The relation among terms will be described in more detail with reference to FIGS. 15A to 15D. FIG. 15A is a schematic view for explaining an inclusion relation among terms in the anatomical classification. FIG. 15B is a schematic view for explaining an inclusion relation among terms in the pathological classification. FIG. 15C is a schematic view for explaining a similarity relation among terms in the anatomical classification. FIG. 15D is a schematic view for explaining a similarity relation among terms in the pathological classification.

FIGS. 15A and 15B schematically show inclusion relations among terms. In the inclusion relation in the anatomical classification, for example, as shown in FIG. 15A, a superordinate concept of "upper lobe" is "lung" and a subordinate concept of "upper lobe" is "upper lobe S1+2." In a similar manner, in the inclusion relation in the pathological classification, for example, as shown in FIG. 15B, a superordinate concept of "adenocarcinoma" is "lung cancer" and a subordinate concept other than "adenocarcinoma" of "lung cancer" is "squamous cell carcinoma."

FIGS. 15C and 15D schematically show similarity relations among terms. In the similarity relation in the anatomical classification, for example, as shown in FIG. 15C, "lung" written in Japanese and "Lung" written in English are in the similarity relation. In a similar manner, in the similarity relation in the pathological classification, for example, as shown in FIG. 15D, "lung cancer" written in Japanese and "Lung Ca" written in English are in the similarity relation.

That is to say, when requested to search for a related term representing the inclusion relation with "upper lobe," the related-term-dictionary archive 2041 returns "lung" as a superordinate concept and "upper lobe S1+2" as a subordinate concept. In a similar manner, when requested to search for a related term representing the similarity relation with "lung cancer," the related-term-dictionary archive 2041 returns "Lung Ca" and "lung tumor" as terms in the similarity relation.

Furthermore, in the case of being unable to specify information (for example, a region name) referring to a region related to the region position and range, corresponding to a description (a text) of the received region information (right lung, left upper lobe or the like), the image region specifying part 204 in the medical image interpretation system relating to the modification retrieves a term in the similarity relation with the received region information as a related term from the related-term-dictionary archive 2041, specifies the position and range of the region corresponding to the related term again, and archives information (for example, a region name) referring to a region in the region position and range together with the related term.

For example, in a case that "Lung (written in English)" is described in the region term extracted by the information extraction processing part 203 as information referring to a lung and the position and range of the region specified by the image region specifying part 204 is determined as "lung (written in Japanese)," these terms are determined as different regions in determination based on only text information. However, by retrieving "lung (written in Japanese)" as a related term in the similarity relation with "Lung (written in English)" from the related-term-dictionary archive 2041 as a processing target, it becomes possible to determine and process these terms as the same region.

Further, in a case that, as compared with the fineness of specification of the region position and range by the image region specifying part 204, more finely divided region names are described in region terms extracted by the information extraction processing part 203, the image region specifying part 204 retrieves a term in the inclusion relation with the received region information as a related term from the related-term-dictionary archive 2041, specifies the position and range of the region corresponding to the related term again, and archives information (for example, a region name) referring to a region in the region position and range together with the related term.

For example, in a case that "upper lobe S1+2" is described in the region term extracted by the information extraction processing part 203 as information referring to a lung and the image region specifying part 204 has not divided "lung" into "upper lobe," which is a superordinate term of "upper lobe S1+2," these terms are determined as different regions and cannot be specified. However, by retrieving "upper lobe" as a superordinate concept of "upper lobe S1+2" from the related-term-dictionary archive 2041 as a processing target, it becomes possible to specify at least as the position and range of "upper lobe" on a diagnostic report.

Although data to be processed is combination of a present examination image, a previous examination image, a present diagnostic report, and a previous diagnostic report in the descriptions of the first and second embodiments, the above descriptions do not restrict combination of data and combination of data to be processed can be changed as necessary.

Finally, the configuration of the respective processing parts and the physical positions of the respective processing parts are not restricted in the apparatus configuration of the medical image interpretation system relating to the first or second embodiment or the modification.

For example, although the medical image and medical record storing part 104 is capable of processing both images and diagnostic reports, it is also possible to separately configure a medical image storing apparatus and a diagnostic report storing apparatus. In this case, such a configuration is preferable that one or more databases and information storage exist, the information extraction processing part 203 and the report processing part 212 are placed in the diagnostic report storing apparatus, and the process controlling part 202 and the image region specifying part 204 are placed in the medical image storing apparatus.

Further, it is possible to configure a stand-alone apparatus by installation into one PC of a medical record generating part 101, a medical image referring part 102, and a medical image and medical record storing part 104. In a case that the apparatus is overloaded, it is possible to independently deploy the information extraction processing part 203 and the image region specifying part 204 as separate apparatuses.

A sentence to be structured can be text data that can be associated with a medical image, for example, in a medical record such as a diagnostic report and a medical chart.

According to the embodiments described above, it becomes possible to, with respect to a region provided with a description of a finding or a diagnosis in a medical record such as a diagnostic report about an examination, display the range of images showing the region or the region position and range on the images showing the region, on the examination image. Besides, it becomes possible to relate the image range or the region position and range to a string showing the finding or the diagnosis indicated in the diagnostic report, or paste into the diagnostic report provided with the description of the finding or the diagnosis. Accordingly, it becomes easy to specify an image relating to a finding or a diagnosis, and it is possible to expect reduction of labor and increase of the efficiency of interpretation in generation and reference of a diagnostic report.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image interpretation system having a medical image referring part, and a medical record storing part configured to store medical records related to medical images and provided with descriptions of findings about the medical images, the medical image interpretation system comprising:
    a memory storing the medical images;
    a process controlling part configured to specify a medical image and extract a medical record of a patient of the medical image;
    an information extraction processing part configured to extract terms for a sentence written in the medical record extracted by the process controlling part, classify the terms into predetermined types to structure the sentence, and extract a at least one region term from the structured sentence;
    an image region specifying part configured to select a region term included in the structured sentence that has a corresponding certainty term having a value of "exist", by checking the certainty term in the structured sentence that includes the region term to specify a set of images extending from a beginning image to a final image, wherein each image in the set of images includes a region corresponding to the selected region term and specify a position and extent of the region in each image in the set of images; and
    an image processing part configured to display at least the position and extent of the region in a visually recognizable manner.

2. The medical image interpretation system according to claim 1, wherein the information extraction processing part further includes a dictionary archive in which dictionary data including a term described in a medical record is archived, and the information extraction processing part is configured to extract the term of a finding included in the dictionary data.

3. The medical image interpretation system according to claim 2, wherein the dictionary data, including a term representing a region, a term representing an imaging observation occurring in the region, and a term representing certainty of the imaging observation, is archived in the dictionary archive, and
    the information extraction processing part is configured to classify the terms extracted from the sentence by kinds of the terms included in the dictionary data and structure with one or more terms classified by the kinds included in one sentence as a series of information.

4. The medical image interpretation system according to claim 3, wherein the information extraction processing part is configured to extract at least information representing certainty of the imaging observation, and extract the at least one region term from the sentence structured under a predetermined condition.

5. The medical image interpretation system according to claim 1, wherein:
    the image region specifying part further has a related-term-dictionary archive in which related-term-dictionary data for managing a relation among terms is archived; and
    a related term related to the region term is extracted from the related-term-dictionary data, and a related set of images that includes a related region corresponding to the related term and a position and extent of the related region on the related set of images showing the related region are specified.

6. The medical image interpretation system according to claim 5, wherein relations among terms indicating an inclusion relation or similarity relation are recorded in the related-term-dictionary data, and inputting a predetermined term makes it possible to retrieve another term indicating the relation with the predetermined term.

7. The medical image interpretation system according to claim 1, wherein the process controlling part is configured to extract the medical record of the patient of the medical image, and the information extraction processing part is configured to structure the sentence written in the extracted medical record.

8. The medical image interpretation system according to claim 1, wherein the information extraction processing part is configured to load a medical record to be archived or having been archived in the memory, and structure a sentence written in the medical record.

9. The medical image interpretation system according to claim 1, wherein the image region specifying part is configured to, by segmentation of extracting an anatomical region from image data acquired by imaging a subject at predetermined intervals in three axis directions, specify the set of images that include the region and the region position and extent on the set of images that include the region.

10. The medical image interpretation system according to claim 1, further comprising a report processing part configured to relate the set of images that include the region and the region position and extent on the set of images that include the region to a sentence written in the medical record from which the region term has been extracted, and make it possible to read out the image range and the region position and extent on the set of images based on the sentence.

11. The medical image interpretation system according to claim 1, further comprising a part configured to paste part or all of images included in the set of images that include the region to a predetermined position of a medical record.

12. The medical image interpretation system according to claim 1, wherein the medical record is a diagnostic report.

* * * * *